United States Patent
Fouts et al.

(10) Patent No.: US 6,245,557 B1
(45) Date of Patent: Jun. 12, 2001

(54) CELL AND PROTEIN HARVESTING ASSEMBLIES AND METHODS

(76) Inventors: Robert P. Fouts, 4401 E. Pleasant Run Parkway. South Dr., Indianapolis, IN (US) 46201; Anthony J. Gardner, 6834 Oxford, Indianapolis, IN (US) 46220

( * ) Notice: Subject to any disclaimer, the term of this patent is extended or adjusted under 35 U.S.C. 154(b) by 0 days.

(21) Appl. No.: 09/478,091

(22) Filed: Jan. 5, 2000

Related U.S. Application Data

(63) Continuation-in-part of application No. 09/345,618, filed on Jun. 30, 1999, now abandoned.

(51) Int. Cl.[7] .................................................. C12M 1/24
(52) U.S. Cl. ...................... 435/304.1; 435/395; 435/396; 435/176
(58) Field of Search ................................ 435/176, 395, 435/396, 304.1

(56) References Cited

U.S. PATENT DOCUMENTS

| | | |
|---|---|---|
| 3,853,712 | 12/1974 | House et al. . |
| 3,941,661 | 3/1976 | Noteboom . |
| 3,948,732 | 4/1976 | Haddad et al. . |
| 4,004,981 | 1/1977 | Hurni et al. . |
| 4,065,359 | 12/1977 | Hurni . |
| 4,317,886 | 3/1982 | Johnson et al. . |
| 4,556,639 | 12/1985 | Izawa et al. . |
| 4,600,694 | 7/1986 | Clyde . |
| 4,734,373 | 3/1988 | Bartal . |
| 4,810,652 | 3/1989 | Witt . |
| 4,829,004 | 5/1989 | Varani et al. . |
| 4,912,058 | 3/1990 | Mussi et al. . |
| 4,962,033 | 10/1990 | Serkes et al. . |
| 5,010,013 | 4/1991 | Serkes et al. . |
| 5,084,393 | 1/1992 | Rogalsky . |
| 5,272,084 | 12/1993 | O'Connell et al. . |
| 5,578,492 | 11/1996 | Fedun . |
| 5,786,215 | 7/1998 | Brown et al. . |

*Primary Examiner*—David A. Redding
(74) *Attorney, Agent, or Firm*—Oldham & Oldham Co., L.P.A.

(57) ABSTRACT

A cell culture assembly is provided. The assembly includes a housing having a first end and a second end and the side wall disposed between the first and second ends. The side wall and the second end define a cell growth chamber and the first end defines an opening for receiving media and starter culture. The assembly includes a continuous elongated ribbon having a leader at one end and a cell growth portion formed into turns and disposed within the chamber. The first end of the ribbon is threaded through an aperture in the side wall with the leader exposed on the outside of the housing. A sealing member is disposed over the leader and the aperture to hermetically seal the aperture. The sealing member is removable to access the leader to pull the ribbon through the aperture. In a preferred embodiment, a squeegee assembly is disposed adjacent the aperture and is configured to apply a squeegee action to the ribbon as the ribbon is pulled through the aperture. Methods are also provided for harvesting cells from a culture bottle, which include providing cell culture media to a container for cell growth, inoculating the media with cells, incubating the cells in the container until sufficient cell growth and multiplication is achieved, removing a sealing member to expose an aperture and pulling the cell growth ribbon through the aperture while applying a squeegee action to remove cells from the ribbon.

25 Claims, 5 Drawing Sheets

CELL AND PROTEIN HARVESTING ASSEMBLIES AND METHODS

This application is continuation-in-part of application Ser. No. 09/345,618, filed Jun. 30, 1999, now abandoned.

FIELD OF THE INVENTION

The present invention relates to the field of cell culturing and cell and protein harvesting. Specifically, the invention relates to enhancing the yield of cells and protein in harvesting productions and experiments.

BACKGROUND OF THE INVENTION

Biotechnology promises to provide economical products to save and enhance lives in fields such as medicine, veterinary science, agriculture and horticulture. For example, several genetically engineered pharmaceuticals expressed from animal cells have recently been approved by the Federal Food and Drug Administration. Although this technology is promising and theoretically unlimited in the benefits that it can provide, it is practically limited by challenges in efficiently and economically achieving large scale cell culture production.

One challenge is that many genetically engineered products cannot be produced without culturing mammalian cells. While bacterial and yeast cells are relatively easy to culture, they are not capable of producing many of the complex molecules that are produced naturally by mammals. Moreover, bacterial and yeast cells often cannot properly fold and process foreign proteins. For example bacterial and yeast cells are not capable of glycosylating proteins. Also, these one-celled organisms are undesirable for many large scale biotechnology processes because, as complete organisms, they are generally not equipped to secrete molecules. In order to harvest protein from these organisms, harsh chemicals or mechanical means must be used to fragment the cells. This must be accomplished without disrupting the delicate three dimensional structure of the protein product. Therefore, mammalian cell cultures are preferred for many biotechnology processes.

Although mammalian cells are preferred or required in many cases, mammalian cells have complex requirements because they are not self-supporting organisms like bacteria and yeast. The culture media must be supplemented with a steady stream of nutrients, hormones and other supplements. Moreover, the cells must be handled gently because the delicate, easily ruptured, cell membrane must remain intact for a mammalian cell to survive. Mammalian cells also grow relatively slowly, dividing only every eighteen to forty-eight hours. In addition, most mammalian cells must be attached to a support or substrate similar to their natural conditions in a living organism.

The requirement for attachment presents further challenges in achieving high yields in biotechnology manufacturing plants. Roller bottles with appropriate culture media are typically employed to culture mammalian cells. The standard roller bottle is generally cylindrically shaped and rotatable about its longitudinal axis. The internal surface provides a surface for the cells to attach and grow. Rotating the bottle keeps the internal surfaces wetted with the liquid media to maintain cell life. The use of these devices, media and procedures has been relatively successful for culturing mammalian cells, but yields have generally been relatively low in a manufacturing sense.

Although it has been recognized for quite some time that it is desirable to increase the yield of cells and cell products, certain constraints have limited success in this endeavor. Roller bottle rotation devices are widely provided in standard sizes. These devices are already in place in many laboratories and production facilities and are designed to accept roller bottles of a specific size and shape. Replacing these with custom devices would be expensive and would destroy the standardization that this field has enjoyed. Therefore, it is generally agreed that the outside configuration of roller bottles should remain constant. As such, attempts to increase the number of cells processed per bottle have focused on modifications to the interior surfaces of the roller bottles and improvements in harvesting the cells once they are grown.

Several patents disclose cell culture vessels with modifications to increase the surface area. For example, U.S. Pat. No. 4,962,033 to Serkes et al. describes a roller bottle with corrugations to increase the internal surface area without changing the exterior dimensions of a standard roller bottle. One limitation of this bottle is that cells that attach to the valleys of the corrugations are more difficult to harvest using a scraper or other physical means. This can be a problem if the use of chemical removal agents such as trypsin is not desired or possible due to the effect of the agent on the desired product. U.S. Pat. Nos. 4,004,981 and 4,065,359 to Humi et al. and 4,600,694 disclose scrapers for physically removing cells from disc stacks. Witt (U.S. Pat. No. 4,810,652) discloses a scraper device for harvesting cells from the interior surface of a conventional roller bottle. This device is designed to improve collection of cells but is not compatible with known increased surface area roller bottles such as the corrugated bottle of Serkes et al.

Other approaches to improve yield have included removable cell supports provided within a cell culture vessel. Some of these provide the advantage of adaptation to the standard roller bottle. However, all of the known devices of this type require the use of a tool or require modifications to the construction of the roller bottle, leading to increased initial expense and inefficiencies during use. For example, U.S. Pat. No. 3,941,661 to Notebloom discloses a plastic spiral roller bottle insert that requires a retractor for removal from the roller bottle. A woven sleeve for a roller bottle, disclosed by Mussi et al., increases surface area available for cell growth but does not provide means for physical removal of cells from the sleeve. The sleeve can be removed from the bottle only if the bottle is specially constructed with a removable top portion. U.S. Pat. No. 3,853,712 to House et al. also discloses a flexible ribbon roller bottle insert for increasing surface area. The roller bottle must be dismantled to access the ribbon. The cell culture vessel is provided in two parts sealed with waterproof tape. The tape is removable to disassemble the vessel to access the ribbon for harvesting cells. Once the ribbon is removed, cells may be harvested enzymatically or by such methods as washing, high speed rotation of the vessel, squeegee action or scraping.

One of the problems with some of these approaches is that they greatly increase the cost of each bottle. Since thousands of bottles are used and discarded on a daily basis, even a small increase in cost is quite expensive to a production or research facility. This expense is further aggravated in some cases by the requirement for time consuming and labor intensive procedures. Moreover, many of these known devices do not readily allow physical removal of cells.

Therefore, a need has remained for cell culture devices and methods that are suited for large scale culturing and physical harvesting of mammalian cells. A need has also remained for mammalian cell culture devices that are inexpensive in construction, efficient in use and adaptable to standard laboratory and production scenarios.

SUMMARY OF THE INVENTION

The present invention provides cell culture devices and methods that address the needs unanswered by the prior art. Briefly describing one aspect of the invention, a cell culture assembly is provided that includes a housing having a first end, a second end and a side wall disposed between the first and second ends. The side wall and the ends define a cell growth chamber. The first end defines an opening for receiving medium and starter culture. The assembly includes a continuous, elongated cell growth ribbon having a leader at one end and a cell growth portion formed into turns and disposed within the chamber. The first end of the ribbon is threaded through an aperture defined in the side wall with the leader exposed on the outside of the housing. A sealing member is disposed over the leader and the aperture to hermetically seal the aperture. To harvest cells, the sealing member is removed and the ribbon is pulled from the chamber through the aperture by applying a pulling action to the leader.

In a preferred embodiment, a squeegee assembly is disposed adjacent the aperture and is configured to apply a squeegee action to the ribbon as the ribbon is pulled through the aperture. In a specific embodiment, the squeegee assembly includes a first squeegee member engaged to one edge of the aperture and a second squeegee member engaged to an opposite edge. The first squeegee member has a tongue member and the second squeegee member defines a groove for receiving the tongue member. The ribbon is threaded between the tongue member and the groove with the leader disposed outside of the aperture.

In another embodiment, the squeegee assembly includes a flap disposed on the side wall adjacent the aperture. The flap has a normally closed position covering the aperture with the sealing member disposed over the flap. The flap is flexible to assume an open position as the ribbon is pulled through the aperture. Preferably, a scraping member is disposed adjacent an edge of the aperture so that the scraping member contacts the surface of the ribbon as the ribbon is pulled through the aperture. In a particular embodiment, the scraping member is a lip member disposed on the edge of the aperture.

In another embodiment, a second flap is disposed on the side wall adjacent a second edge of the aperture. Each of the flaps have a normally closed position covering the aperture with the sealing member disposed over the flaps. Each flap is flexible to assume an open position as the ribbon is pulled through the aperture. In some embodiments, a scraping member is disposed on one or both of the flaps and the scraping members are positioned to cooperate to provide a squeegee movement to the ribbon as the ribbon is pulled through the aperture. The flaps can be positioned where one overlaps the other or so that the projecting edges of the flaps approach each other when the flaps are in the closed position. In other embodiments, lip members are disposed on each of the projecting edges of the flaps.

In preferred embodiments, the ribbon is ion charged to promote cell adherence. The ribbon is preferably folded into turns to provide maximum surface area for supporting cell growth. In one embodiment the ribbon is folded to form a spiral cross-section. Preferably, the opposite end of the ribbon is attached to a spiral frame. The frame supports the ribbon in a desirable configuration for cell growth and multiplication. In another embodiment the ribbon is pleated. In other embodiments, the ribbon includes a stop member disposed on an opposite end of the ribbon within the housing. The stop member has a dimension that is larger than a dimension of the aperture. In some embodiments, the stop member is an enlarged section of the ribbon that will not move through the aperture.

The present invention also provides methods for harvesting cells from a culture bottle. The methods includes providing cell culture media to the chamber of an assembly of this invention, inoculating the media with cells, incubating the cells in the container until sufficient cell growth and multiplication is achieved, removing the sealing member to expose the leader and pulling the ribbon through the aperture while applying a squeegee action to the ribbon to remove cells from the ribbon. After the ribbon has been pulled through the aperture, the methods also include scraping an internal surface of the chamber to harvest cells from the inner surface of the chamber after pulling the ribbon through the aperture.

Accordingly, it is one object of the invention to provide improved cell culture devices and methods. These and other objects, advantages and features are accomplished according to the devices and methods of the present invention.

DESCRIPTION OF THE PREFERRED EMBODIMENTS

Figure 1:
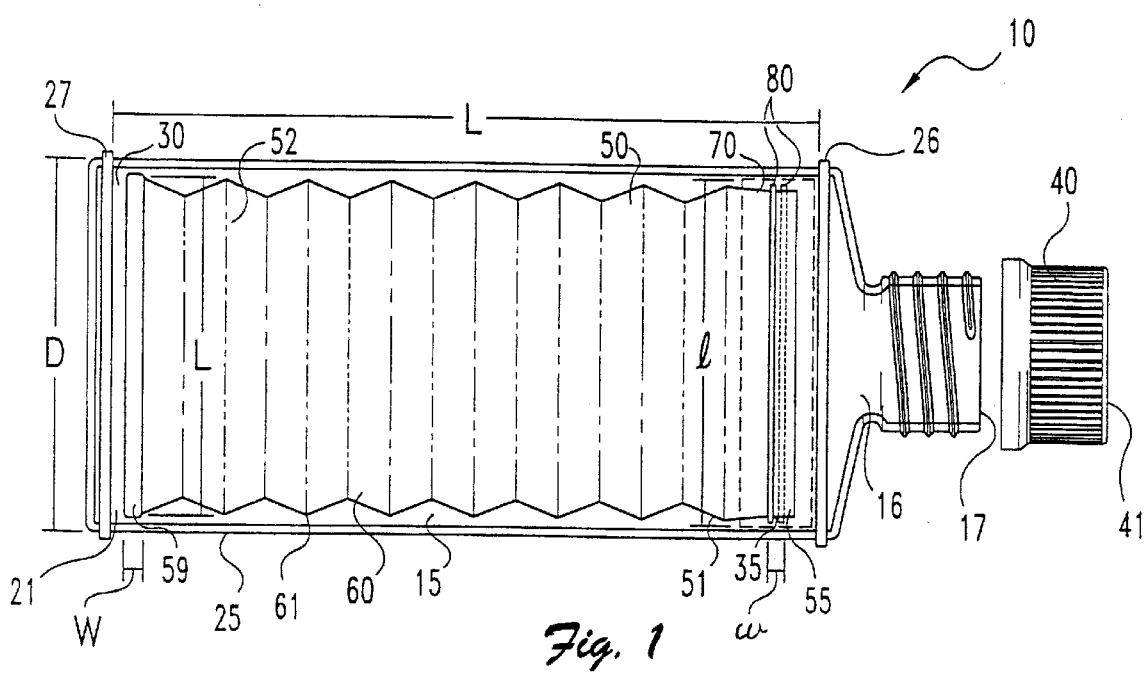
FIG. 1 is a side elevational view of a container assembly according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides cell culture devices and methods that are suited for large scale culturing and physical harvesting of mammalian cells. The devices of this invention are inexpensive in construction, efficient in use and adaptable to standard laboratory and production scenarios.

A cell culture assembly 10 of the present invention is depicted in FIG. 1. The assembly includes a roller bottle 15 or housing having a first end 16 and a second end 21 with a side wall 25 disposed between the first end 16 and the second end 21. The side wall 25 and the second end 21 define a cell growth chamber 30. The first end 16 defines an opening 17 for receiving media and starter culture. A cap 40 with a cap vent 41 is provided for closing the opening 17 at the first end 16. Roller traction strips 26, 27 are provided at each end 16, 21 respectively. Preferably, the roller bottles 15 of the present invention are of a standard size and shape. For example, in the specific embodiment, the length L between the roller traction strips 26, and 27 is about 230 mm while the diameter D is 115 mm. Standard roller bottles are commercially available and can be modified according to this invention. The roller bottles of this invention may also be manufactured using known plastic molding processes, such as blow molding.

The present invention achieves higher yields using roller bottles of standard dimensions by employing a continuous, elongated growth film or ribbon 50. The ribbon is composed of any biocompatible material to which cells will adhere and which will support cell growth. For disposable assemblies, certain polyesters and other polymers may be used to construct the ribbons of this invention. However, any suitable non-toxic material having sufficient strength, low weight and cost is contemplated. Optionally, the ribbon is composed of a polymer rigid enough to be self supporting while being pliable enough to be easily removed from the roller bottle 15. In preferred embodiments, ribbon 50 is ion charged to attract cells. The ribbon preferably has a thickness of between about 10 to 1000 microns.

Ribbon 50 includes a leader 55 at one end 51 of the ribbon 50. A cell growth portion 60 of the ribbon 50 is formed into turns and is disposed within the chamber. Any suitable configuration of the ribbon 50 that will maximize the surface area available for cell attachment is contemplated. In FIG. 1 the ribbon 50 is pleated to form numerous folds 61. In other embodiments, the ribbons of this invention may be folded to form a spiral cross-section, a semi-circular coil cross-section, or any other high surface area configuration, so long as the ribbon can easily be removed through the aperture of the roller bottle.

Figure 2:
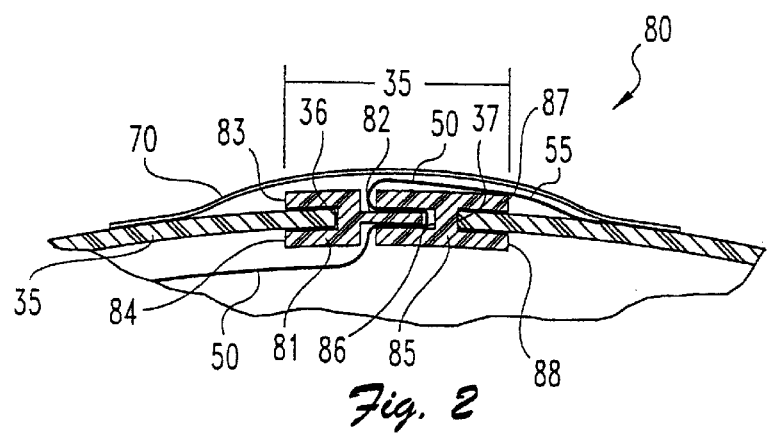
FIG. 2 is a side cross-sectional view of a squeegee assembly according to this invention.

The growth ribbon 50 can be conveniently accessed from the outside of the bottle through aperture 35 defined in the sidewall 25 of the bottle 15 as illustrated in FIG. 2. The first end 51 of the ribbon 50 is threaded through the aperture 35 with the leader 55 exposed outside of the housing 15. A sealing member 70 is disposed over the leader 55 and the aperture 35 to hermetically seal the aperture 35. Preferably, the sealing member is fluid impermeable tape. The sealing member 70 is manually removable to access the leader 55. The leader 55 is conveniently provided for grasping to pull a portion of the cell growth portion 60 of the ribbon 50 from the chamber 30 through the aperture 35.

In some embodiments, an opposite end 52 of the ribbon 50 includes a stop member 59 that is disposed within the housing 15. As shown in FIG. 1, stop member 59 has a dimension that is larger than a dimension of the aperture 35. For example stop member 59 may have a width W that is wider than the width of w of aperture 35 or a length L that is longer than the length l of the aperture 35.

In preferred embodiments, a squeegee assembly 80 is incorporated into the assembly 10 to simultaneously apply a squeegee action to the ribbon 50 as the ribbon 50 is pulled through the aperture 35. As shown in FIG. 2, squeegee assembly 80 includes a first squeegee member 81 engaged to an edge 36 of aperture 35. The first squeegee member 81 in this embodiment includes a tongue 82. The first squeegee member 81 cooperates with a second squeegee member 85 that is also engaged to an opposite edge 37 of the aperture 35. The second squeegee member 85 defines a groove 86 for receiving the tongue 82 of the first squeegee member 81. Ribbon 50 is threaded between tongue member 82 and groove 86 with the leader 55 disposed outside of the aperture 35. As ribbon 50 is pulled through the squeegee assembly 80, cells are removed from ribbon 50. After ribbon 50 has been pulled through squeegee assembly 80, cells may be collected from inside the chamber 30.

In some embodiments, tongue 82 is relatively flexible, having a lower durometer than the remainder of the squeegee assembly 80. The gap between the tongue 82 and groove 86 is dimensioned large enough so that the ribbon 50 can be pulled through the aperture 35 smoothly without much physical exertion yet small enough to achieve a squeegee action. To achieve this function, squeegee assembly 80 is constructed of any suitable material, preferably silicon. The squeegee assemblies of this invention can be manufactured using known methods, such as injection molding.

The particular means for engaging the squeegee assembly 80 to the side wall 25 of the roller bottle 15 is not critical. As shown in FIG. 2 both the first member 81 and the second member 85 each have a pair of prongs 83, 84, 87, 88. The prongs engage the edges 36, 37 of opening 35 so that the squeegee assembly 80 is securely fixed to the side wall 25.

Figure 3:
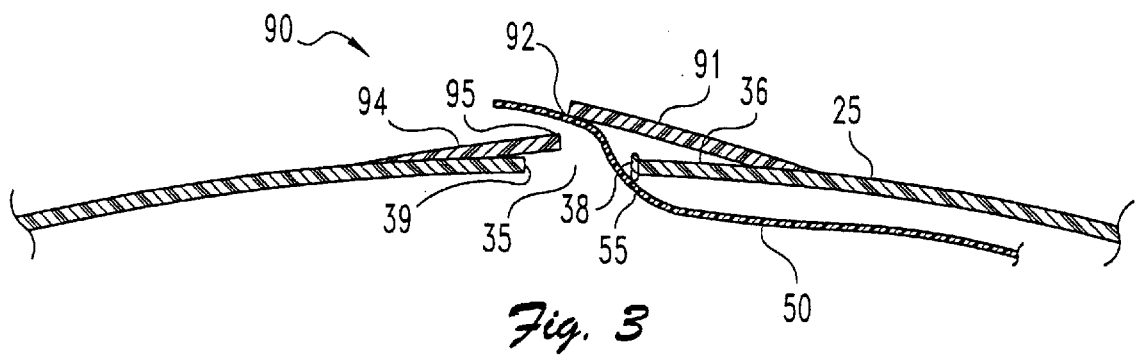
FIG. 3 is a side cross-sectional view of squeegee assembly according to one embodiment of this invention.

In another embodiment depicted in FIG. 3, squeegee assembly 90 includes a flap 91 disposed on the side wall 25 adjacent the aperture 35. Flap 91 has a normally closed position covering the aperture 35 when the sealing member is disposed over the flap 91. Flap 91 is flexible to assume an open position as the ribbon 50 is pulled through the aperture 35. Preferably, a scraping member will be disposed adjacent an edge 36 of the aperture 35. The scraping member contacts the surface of the ribbon 50 as the ribbon is pulled through the aperture. In one embodiment the scraping member is a lip 38 disposed on an edge 36 of the aperture 35. In other embodiments an edge 92 of the flap 91 is also provided as a scraping member.

In some embodiments a squeegee assembly includes a second flap 94 disposed on the side wall 25 adjacent a second edge 37 of the aperture 35. Both of the flaps 91, 94 are in the normally closed position covering the aperture 35 when the sealing member 70 is disposed over the flaps 91, 94. Each of the flaps 91, 94 are flexible to assume an open position as shown in FIG. 3 as the ribbon 50 is pulled through the aperture 35. Flap 94 may also be provided with the scraping edge 95 similar to the scraping edge 92 of flap 91.

Figure 4:
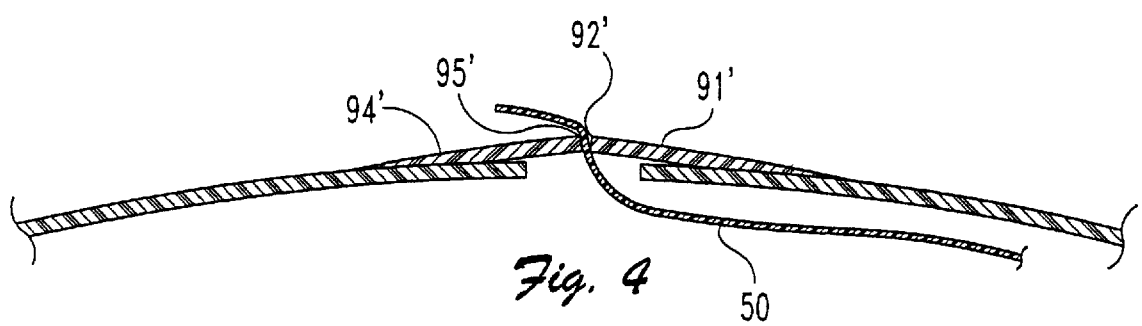
FIG. 4 is a side sectional view of another squeegee assembly according to this invention.

In the embodiment shown in FIG. 3, first flap 91 overlaps second flap 94. In another embodiment depicted in FIG. 4, first and second flaps 91', 94' are each of a length where such that edges 92', 95' approach one another in both the open and closed positions in order to provide a squeegee action to ribbon 50.

Figure 5:
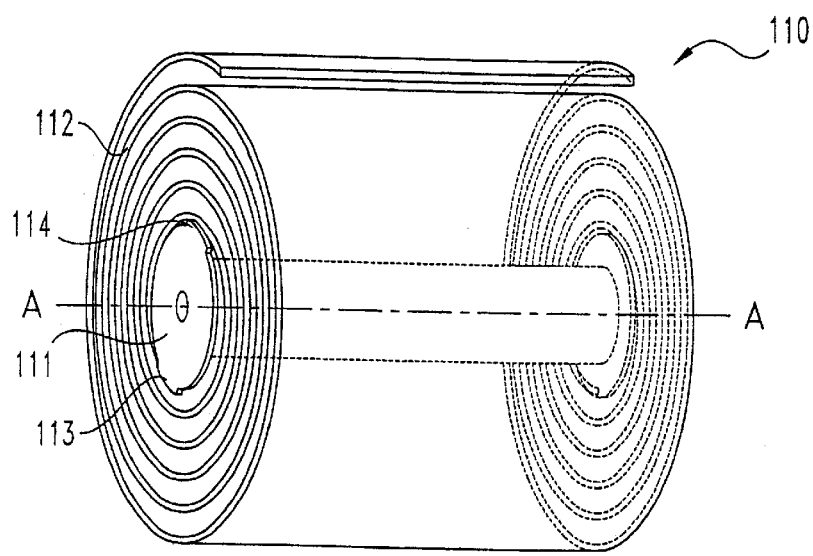
FIG. 5 is a side elevational view of a spiral frame according to this invention.
Figure 6:
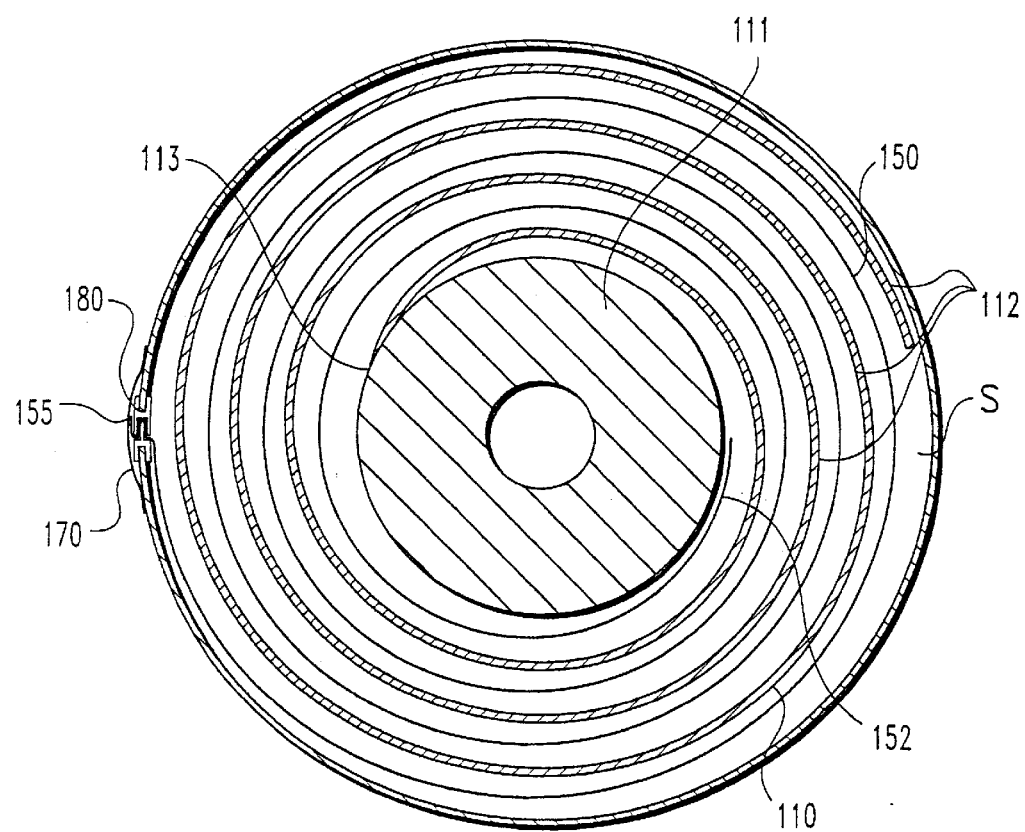
FIG. 6 is a cross-sectional view of an assembly with a ribbon supported by a spiral frame.

For some ribbon configurations, it is preferable to employ a frame that provides support for the ribbon, such as ribbon 150 in FIG. 6. The frames define channels for receiving the ribbon 150 to form turns or convolutions. As shown in FIGS. 5 and 6, a spiral frame 10 forms a continuous channel 109 for supporting ribbon 150 in the spiral configuration. Channel 109 also provides an advantageous inner layer separation S between each layer of ribbon 150. In one specific embodiment, the inner layer separation S is about 2 mm which provides enough space for culture media and cell growth on the ribbon 150. The frames of this invention can be made of any suitable biocompatible material that will hold its desired shape. Various polymers are contemplated and the frame can be manufactured using known methods, such as injection molding.

The Frame 110 in FIG. 5 has a center base portion 111 that supports a spiral body 112. Base portion 111 engages spiral body 112 at an engagement point 113. As shown in FIG. 6, ribbon 150 is threaded through channel 109 within the spiral frame 110 with the opposite end 152 of ribbon 150 adjacent the spiral body 112. Ribbon 150 is wound along the spiral body 112 until it exits the roller bottle 115 through the aperture 135. Leader 155 extends through the squeegee assemble 180 and is sealed along with the aperture 135 with sealing member 170. When sealing member 170 is removed and a pulling force is applied to leader 155, ribbon 150 unrolls from its spiral configuration so that it can be pulled through aperture 135.

Figure 7:
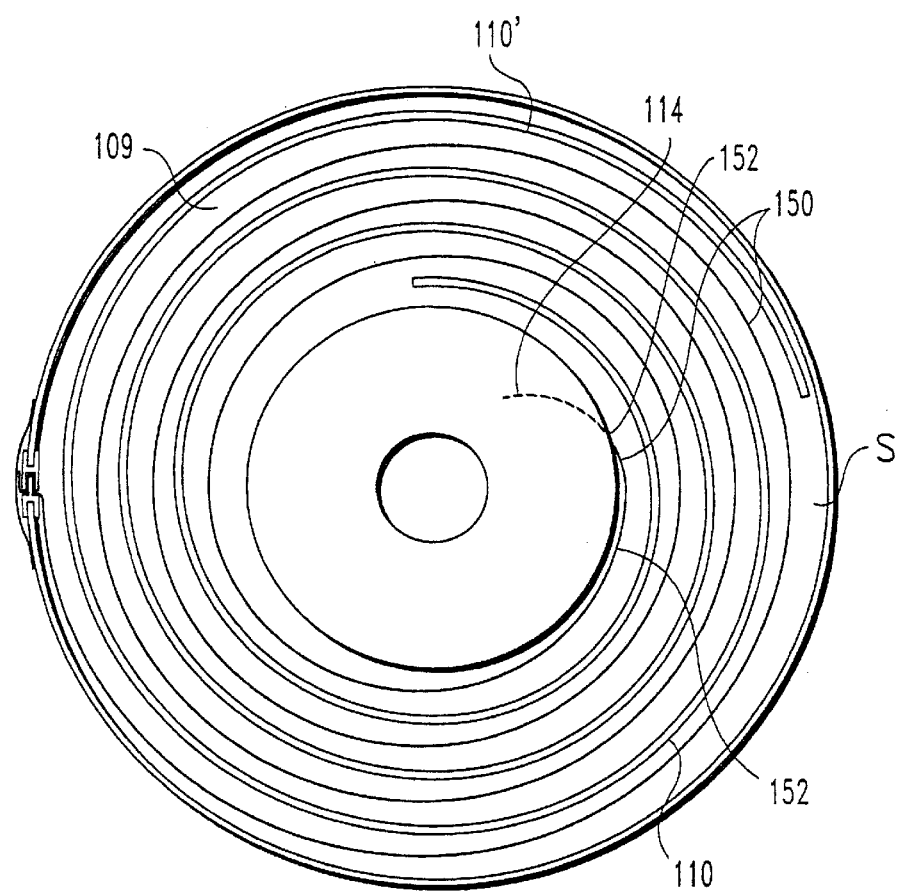
FIG. 7 is a cross-sectional view of an assembly with a ribbon supported by a spiral frame.

In another embodiment depicted in FIG. 7, ribbon 150 is wedged into a slot 114 defined in an outer surface of the base 111'. Ribbon 150 is releasably engaged to frame 110' so that end 152 of the ribbon 150 will be released from the slot 114 upon receiving the pulling force applied to the leader 155.

Figure 8:
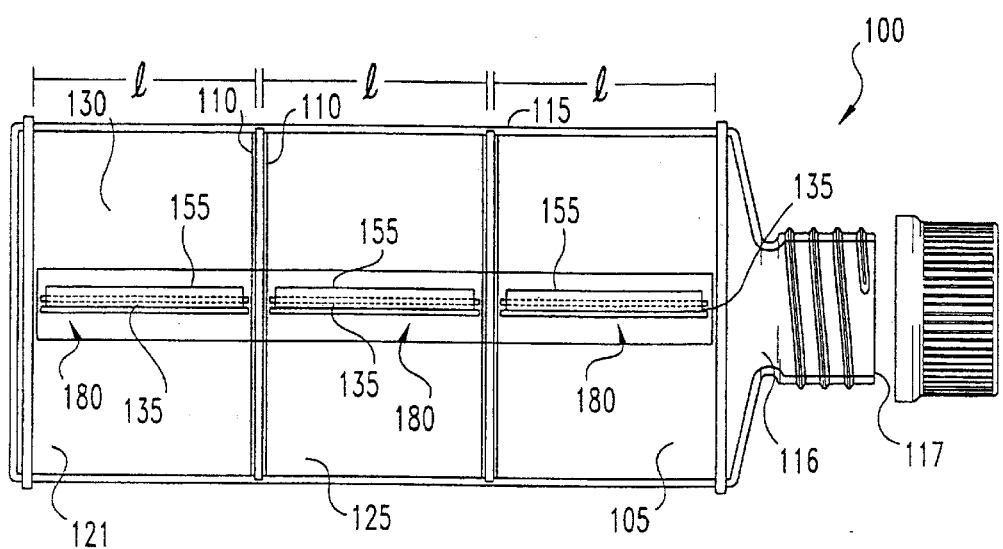
FIG. 8 is a side elevational view of another embodiment of this invention.

In the embodiment depicted in FIG. 8, the assembly 100 is provided with more than one aperture 135 and squeegee assembly 180. In this arrangement, the length 1 of each ribbon 150 is limited to a manageable length for ease of pulling the ribbon 150 through its corresponding aperture 135. Preferably each aperture-assembly pair corresponds to a spiral frame and ribbon pair as shown in FIG. 6.

Figure 9:
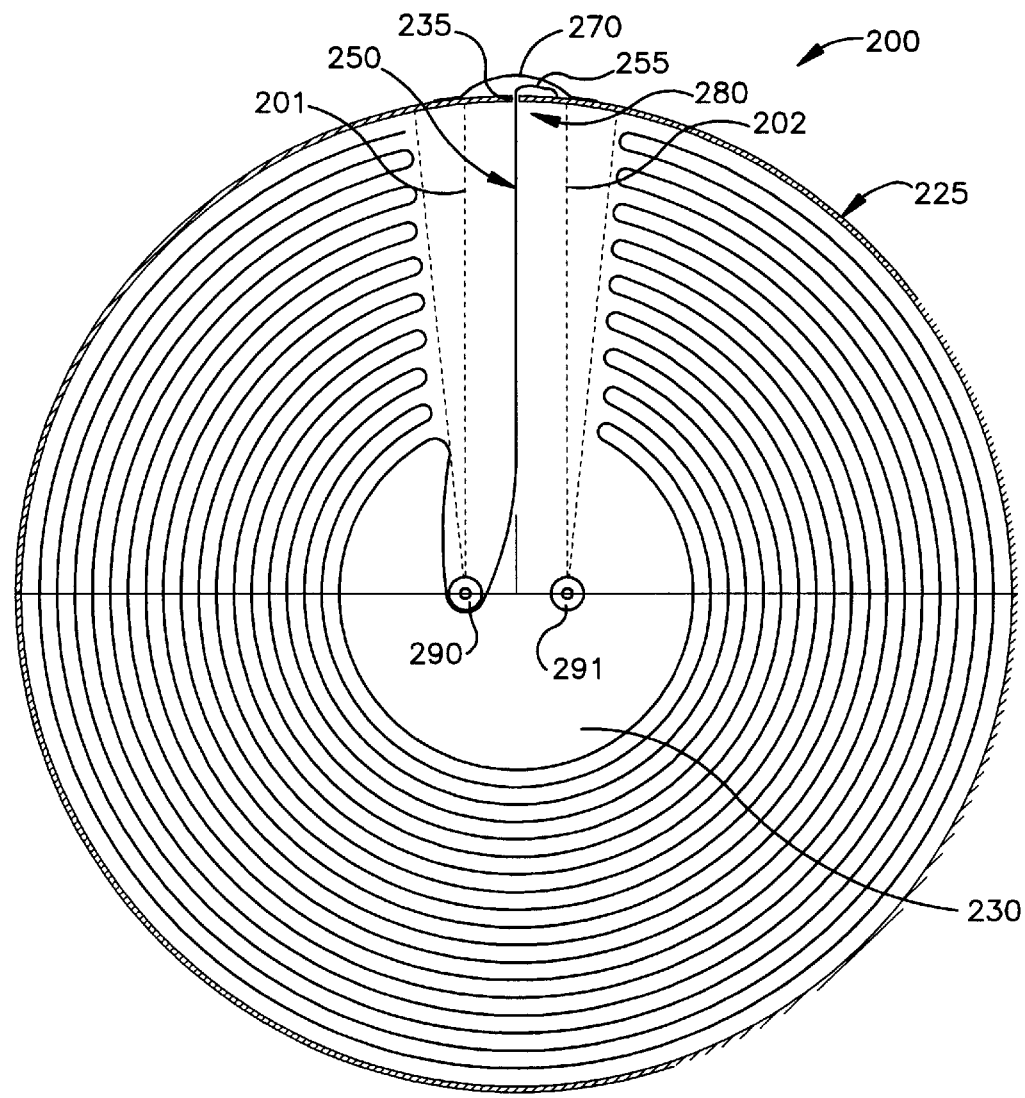
FIG. 9 is a top view of another embodiment of this invention.

Referring now to FIG. 9, there is shown another embodiment 200. In this embodiment, ribbon 250 is placed within cell growth chamber 230 in a semi-circular coil pattern. In this pattern, there is placed sixteen to eighteen layers of ribbon 250 with a 2 millimeter layer of separation between each of the ribbon layers. However, the number of layers and the space of separation may be altered depending on the application and is not to be considered a limitation of this invention. Optionally, rounded teeth or ribs may be formed on the outer surface of the supports 201 and 202 to aid in optimally spacing the folds of ribbon 250. Ribbon 250 is placed within the cell growth chamber 230 in a manner that the first end 251 of ribbon 250 is positioned on roller 290 or 291 and directed toward aperture 235 formed in the sidewall of the cell culture assembly 200. Ribbon 250 has a leader 255 at one end 251 of ribbon 250. The first end 251 of ribbon 250 is threaded around roller 290 or 291 and through the aperture 235 with the leader exposed outside of the sidewall 225. Roller 290 or 291 aid in guiding ribbon 250 from its coiled position toward the aperture 235. A sealing member 270 is disposed over the leader 255 and the aperture 235 to hermetically seal the aperture 235. As with the other embodiments, herein disclosed, sealing member 270 is preferably fluid impermeable tape.

Also shown in the embodiment of FIG. 9, is squeegee assembly 280. Squeegee assembly 280 can be formed as the any of the various squeegee assemblies described herein. As ribbon 250 is pulled through squeegee assembly 280, cells are removed from ribbon 250 and can then be collected from inside the cell growth chamber 230.

Figure 10:
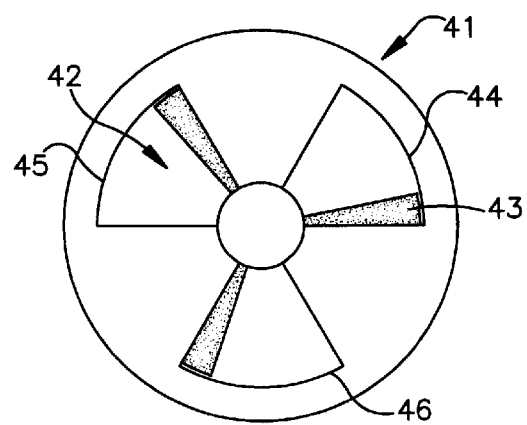
FIG. 10 is a top view of the vent cap of the present invention.

As shown in FIG. 10, cap 40 may optionally have a vent cap 41 to allow for venting of the various embodiments of the cell culture assemblies of the present invention. Cap 40 is provided with a sliding vent cover 43 that allows for selectively opening vents 44, 45, and 46 of vent cap 41. Vent cap 41 has a hydrophobic membrane that seals off vents 44, 45 and 46 when said vents are in the closed position. For most applications, a 0.2 micron membrane is used but this application should not be so limited, as any membrane appropriate for the application may be used.

The present invention also provides methods for culturing and harvesting cells. The methods include providing cell culture media to an assembly for cell growth of this invention and inoculating the media with cells according to methods known in the art. The particular media and cells employed will depend upon the desired product. The cells will tend to adhere to the cell growth ribbon. The cells are then incubated in the assembly until sufficient cell growth and multiplication is achieved. Preferably, the roller bottle will be incubated at a preferred temperature for the cells and will be constantly rolled within the incubator so that the cells are constantly nourished, hydrated and oxygenated. Roller speeds, temperature and length of incubation are known for various cells. In cases where these parameters are not known, they can be determined by one skilled in the art.

Once sufficient cell growth and multiplication is achieved, the roller bottle is removed from the incubator. The sealing member is removed from the bottle to expose the leader portion of the ribbon. The leader is manually grasped and a pulling force is applied to the leader. The pulling force pulls the ribbon through the aperture. Cells can then be removed from the ribbon after the ribbon is removed from the culture bottle. Preferably the cells are removed before or simultaneously with the removal of the ribbon from the growth chamber of the assembly. In preferred embodiments the methods include applying a squeegee action to remove cells from the ribbon while the ribbon is pulled through the aperture. After the ribbon is removed, the media and cells can be removed from the bottle through the opening in the first end of the bottle. The internal surface of the chamber can be scraped to harvest further cells from the inner surface of the bottle.

In some methods that employ a stop member, the ribbon can be rethreaded into the chamber so that the entire assembly can then be sterilized and reused. However, the assemblies of this invention can be manufactured so inexpensively that it is contemplated that these assemblies will be disposable.

The present invention economically and conveniently provides cell culture assemblies and methods. This invention increases yields in processes that rely on mammalian cell cultures. This invention employs culture bottles having standard outside dimension so that standardization in the laboratory and plant are not sacrificed for the sake of improved yields.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A cell culture assembly, comprising:
    a housing defining a cell growth chamber and having a first end and a second end and a sidewall disposed between said first and second ends, said sidewall defining an aperture; and
    a continuous, elongated ribbon having a leader at one end and a cell growth portion disposed within said chamber, said one end of said ribbon threaded through said aperture with said leader exposed outside of said housing for pulling said ribbon from said chamber through said aperture.

2. The assembly of claim 1, wherein said first end defines an opening for receiving media and starter culture into the chamber.

3. The assembly of claim 2, further comprising a cap which is fastened about said opening for sealing said opening.

4. The assembly of claim 3, wherein said cap further comprises a vent assembly which is selectively opened or closed to allow for selective venting of said assembly.

5. The assembly of claim 1, further comprising a sealing member disposed over said leader and said aperture for hermetically sealing said aperture, said sealing member removable to access said leader.

6. The assembly of claim 1, further comprising a squeegee assembly disposed adjacent said aperture, said squeegee assembly configured to apply a squeegee action to said ribbon as said ribbon is pulled through said aperture.

7. The assembly of claim 6, wherein said squeegee assembly includes
a first squeegee member engaged to an edge of said aperture, said first squeegee member having a tongue; and
a second squeegee member engaged to an opposite edge of said aperture, said second squeegee member defining a groove for receiving said tongue, said ribbon threaded between said tongue and said groove, with said leader disposed outside of said aperture.

8. The assembly of claim 1, further comprising:
a frame member disposed within said chamber, said frame member having a body forming a channel for receiving said ribbon and wherein said ribbon is threaded through said channel to form said tuns.

9. The assembly of claim 8, wherein said body is shaped to form a spiral channel.

10. The assembly of claim 1, further comprising:
a flap disposed on said sidewall adjacent said aperture, said flap having a normally closed position covering said aperture with said sealing member disposed over said flap, said flap flexible to assume an open position as said ribbon is pulled through said aperture.

11. The assembly of claim 10, further comprising:
a scraping member disposed adjacent an edge of said aperture, said scraping member contacting a surface of said ribbon as said ribbon is pulled through said aperture.

12. The assembly of claim 11, wherein said scraping member is a lip member disposed on an edge of said aperture.

13. The assembly of claim 10, further comprising:
a first flap disposed on said sidewall adjacent a first edge of said aperture;
a second flap disposed on said sidewall adjacent a second edge of said aperture;
each said flap having a normally closed position covering said aperture with said sealing member disposed over said flaps, each said flap flexible to assume an open position as said ribbon is pulled through said aperture.

14. The assembly of claim 13, further comprising:
a scraping member disposed on one of said flaps, said scraping member contacting a surface of said ribbon as said ribbon is pulled through said aperture.

15. The assembly of claim 14, further comprising:
a second scraping member disposed on the other of said flaps, said second scraping member contacting a surface of said ribbon as said ribbon is pulled through said aperture, said scraping member and said second scraping member positioned to cooperate to provide a squeegee movement to said ribbon as said ribbon is pulled through said aperture.

16. The assembly of claim 13 wherein said second flap overlaps said first flap.

17. The assembly of claim 13, wherein each said first and second flaps include a projecting edge and said projecting edges approach each other when said flaps are in the closed position.

18. The assembly of claim 1, wherein said ribbon is ion charged.

19. The assembly of claim 1, wherein said ribbon is folded to form a spiral cross-section.

20. The assembly of claim 1, wherein said ribbon is folded to form a semicircular coil cross-section.

21. The assembly of claim 1, wherein said sealing member is fluid impermeable tape.

22. The assembly of claim 1, wherein said leader is fastened to an outside surface of said sidewall with said sealing member when said sealing member is disposed over said aperture.

23. The assembly of claim 1, wherein said ribbon has an opposite end disposed within said housing, said ribbon including a stop member disposed on said opposite end and having a dimension larger than said aperture.

24. A method for harvesting cells from a culture bottle, comprising:
providing cell culture media to an assembly for cell growth of claim 1;
inoculating the media with cells;
incubating the cells in the assembly until sufficient cell growth and multiplication is achieved;
after sufficient cell growth and multiplication is achieved, removing the sealing member to expose the leader;
after the aperture is exposed, pulling the ribbon through the aperture while applying a squeegee action to remove cells from the ribbon.

25. The method of claim 22, further comprising: scraping an internal surface of the chamber to harvest cells from the inner surface after pulling the ribbon through the aperture.

* * * * *